United States Patent [19]

Kajihara et al.

[11] Patent Number: 5,690,726
[45] Date of Patent: Nov. 25, 1997

[54] DIMETHYLALUMINUM HYDRIDE COMPOSITION, PROCESS FOR PRODUCING THE SAME AND METHOD OF REDUCING VISCOSITY OF DIMETHYLALUMINUM HYDRIDE

[75] Inventors: Kazuhisa Kajihara; Tadaaki Yako, both of Niihama, Japan

[73] Assignee: Sumitomo Chemical Company, Ltd., Osaka, Japan

[21] Appl. No.: 764,623

[22] Filed: Dec. 11, 1996

Related U.S. Application Data

[63] Continuation-in-part of Ser. No. 637,904, Apr. 26, 1996, abandoned.

[30] Foreign Application Priority Data

Apr. 28, 1995 [JP] Japan ................................. 7-106758
Jan. 30, 1996 [JP] Japan ................................. 8-014117

[51] Int. Cl.$^6$ ........................................................ C07F 5/06
[52] U.S. Cl. ................................................... 106/287.17
[58] Field of Search ........................................ 106/287.17

[56] References Cited

U.S. PATENT DOCUMENTS 2,765,329 10/1956 Lindsey, Jr. .
3,453,093 7/1969 Kobetz et al. .
4,897,500 1/1990 Hui et al. ............................. 556/187
4,924,019 5/1990 Hui et al. .

FOREIGN PATENT DOCUMENTS 763824 12/1956 United Kingdom .
774516 5/1957 United Kingdom .

OTHER PUBLICATIONS

Finholt et al., *J. Am. Chem. Soc.*, vol. 69, pp. 1199–1203 (1947) No Month Avail.
Wartik et al., *J. Am. Chem. Soc.*, vol. 75, pp. 835–839 (1953).
Barbaras et al., *J. Am. Chem. Soc.*, vol. 73, pp. 4585–4590 (1951) No Month Avail.

*Primary Examiner*—David Brunsman
*Attorney, Agent, or Firm*—Birch, Stewart, Kolasch & Birch, LLP

[57] ABSTRACT

The present invention provides a dimethylaluminum hydride composition having a low viscosity at normal temperature, comprising dimethylaluminum hydride and at least one Lewis base in an amount of from about 0.001 to about 10% by weight based on dimethylaluminum hydride. The resulting dimethylaluminum hydride composition is superior in handling properties. The present invention also provides a method for reducing the viscosity of dimethylaluminum hydride.

24 Claims, No Drawings

DIMETHYLALUMINUM HYDRIDE COMPOSITION, PROCESS FOR PRODUCING THE SAME AND METHOD OF REDUCING VISCOSITY OF DIMETHYLALUMINUM HYDRIDE

This application is a continuation-in-part of application Ser. No. 08/637,904 filed on Apr. 26, 1996, now abandoned, the entire contents of which are hereby incorporated by reference.

FIELD OF THE INVENTION

The present invention relates to a dimethylaluminum hydride composition, a process for producing the same and a method of reducing the viscosity of dimethylaluminum hydride. More particularly, it relates to a dimethylaluminum hydride composition having a low viscosity at normal temperature, which is superior in handling properties, a process for producing the same and a method of reducing the viscosity of dimethylaluminum hydride.

BACKGROUND OF THE INVENTION

Dimethylaluminum hydride (hereinafter abbreviated to "DMAH") is mainly used as an aluminum raw material in a chemical vapor deposition process (e.g. metal organic chemical vapor deposition, metal organic molecular beam epitaxy, etc.). In the process, the dimethylaluminum hydride is introduced into a vapor deposition device according to a method (1) comprising supplying a carrier gas such as hydrogen whose flow is controlled by a mass flow controller into a DMAH solution in a storage container, bubbling the solution by the carrier gas and then introducing the bubbled carrier gas saturated with DMAH into a vapor deposition device; method (2) comprising directly heating a DMAH storage container to evaporate DMAH at a temperature below its boiling point and introducing DMAH vapor into a vapor deposition device while controlling the flow using a mass flow controller; and method (3) comprising pressurizing a DMAH storage container using a carrier gas such as hydrogen or nitrogen, transferring DMAH in the container to an evaporator in the liquid state, heating DMAH in the evaporator to evaporate DMAH and supplying a carrier gas to introduce DMAH vapor into a vapor deposition device.

However, DMAH has the following problems on use. That is, it is difficult to transfer DMAH from a storage container to the device to be used and to conduct bubbling at the time of the vapor deposition reaction because DMAH has high viscosity, i.e., from several thousands to several ten thousands at room temperature. From the manufacturing point of view, it is difficult to transfer or deactivate DMAH as compared with other normal organic aluminums because DMAH has a self-ignition property and high viscosity. A method of reducing the viscosity of dimethylaluminum hydride has thus been desired.

SUMMARY OF THE INVENTION

Under these circumstances, the present inventors have intensively studied methods of reducing the viscosity of dimethylaluminum hydride even at normal temperature. As a result, it has been found that a remarkable effect of reducing the viscosity of DMAH is obtained when a very small amount of a Lewis base is added to DMAH. Thus, the present invention has been accomplished.

An object of the present invention is to provide a dimethylaluminum hydride composition having a low viscosity at normal temperature, which is easily handled.

Another object of the present invention is to provide a process for producing the same.

Still another object of the present invention is to provide a method of reducing the viscosity of dimethylaluminum hydride.

These objects as well as other objects and advantages of the present invention will become apparent to those skilled in the art from the following description.

In summary, the present invention provides a dimethylaluminum hydride composition, comprising dimethylaluminum hydride and at least one Lewis base in an amount of about 0.001 to about 10% by weight of dimethylaluminum hydride, and a process for producing the same.

The present invention further provides a method of reducing the viscosity of dimethylaluminum hydride at normal temperature (25° C.), which comprises adding at least one Lewis base to dimethylaluminum hydride in an amount of about 0.001 to about 10% by weight of dimethylaluminum hydride.

DETAILED DESCRIPTION

The present invention relates to a DMAH composition comprising dimethylaluminum hydride and a Lewis base in an amount of from about 0.001 to about 10% by weight, usually from about 0.005 to about 10% by weight, preferably from about 0.01 to about 10% by weight, more preferably from about 0.03 to about 1% by weight, based on DMAH, wherein the viscosity of the DMAH composition at normal temperature (25° C.) is not more than about 5000 mPa.s ("mPa.s" is equivalent to "centipoise"). In the case that transfer is performed in the liquid state, the viscosity of the DMAH composition is usually about 2000 to about 5000 mPa.s. In the case that transfer of the composition is performed in the vapor, state, the viscosity of the DMAH composition is usually not more than about 2000 mPa.s, normally not more than about 1000 mPa.s, and preferably from about 10 to about 500 mPa.s. Such a composition is extremely superior in handling properties.

According to a typical process for producing the DMAH composition, a Lewis base is added in the amount of from about 0.001 to about 10% by weight, usually from about 0.005 to about 10% by weight, preferably about 0.01 to about 10% by weight, more preferably from about 0.03 to about 1% by weight based on DMAH, followed by mixing.

The DMAH to be used is not a specific one, and is DMAH having a viscosity of more than about 5000 mPa.s at normal temperature, normally from several thousands to several ten thousands mPa.s, particularly from about 7000 to about 20000 mPa.s and more particularly from about 7000 to about 10000 mPa.s at normal temperature (25° C.), which is commercially available or obtainable by a known synthetic method, for example, by reacting dimethylaluminum chloride with an alkali metal hydride or by reacting trimethylaluminum with lithium aluminum hydride (e.g., U.S. Pat. No. 4,924,019 and J. Am. Chem. Soc. 75, 835 (1953)).

The Lewis base used in the present invention refers to a compound having at least one single pair of electrons and which can be coordinated with DMAH. Examples of the Lewis base include organic compounds containing at least one element selected from the element groups Vb and VIb in the Periodic Table and organic compounds containing at least one element selected from N, P, As, O and S. Specific examples thereof include ethers such as diethyl ether, dibutyl ether, methyl butyl ether, anisole, diphenyl ether, benzyl ether, dimethoxyethane, diethoxyethane, tetrahydrofuran and dioxane; amines such as triethylamine, trioctylamine, dimethylpropylamine, dimethyldodecylamine, dimethylaminotrimethylsilane, dimethylallylamine, diisopropylethylamine, dimethylaniline, benzylethylaniline, tetramethylethylenediamine, tetramethyldiaminopropane and tetramethylhexamethylenediamine; heterocyclic compounds having at least one nitrogen atom in a ring structure such as pyridine, dimethylaminopyridine, collidine, pyrazine, dimethylpyrazine, pyrazole, quinoline, isoquinoline, triazine, triazole, quinaldine, imidazole and benzylmethylimidazole; sulfides such as dimethyl sulfide, diethyl sulfide and diphenyl sulfide; heterocyclic compounds having at least one sulfur atom in a ring structure such as thiophene; phosphines such as triethylphosphine and triphenylphosphine; organoarsines such as triethylarsine, etc. Among them, diethyl ether, dibutyl ether, tetrahydrofuran, triethylamine, dimethyldodecylamine and dimethylaniline are preferred.

The Lewis base may be normally added to DMAH at normal temperature in an amount of from about 0.001 to about 10% by weight, usually from about 0.005 to about 10% by weight, preferably from about 0.01 to about 10% by weight, more preferably from about 0.03 to about 1% by weight of DMAH, followed by mixing. After the operation, there can be obtained a DMAH composition having a viscosity of not more than about 5000 mPa.s, preferably 2000 mPa.s even at normal temperature (25° C.) under atmospheric pressure, which is superior in handling properties.

The upper limit of the amount of the Lewis base may be usually decided by the permissible purity of DMAH as limited by its application.

When the Lewis base is added in an amount of from about 0.001 to about 10% by weight, preferably from about 0.005 to about 1% by weight, more preferably about 0.01 to about 1% by weight, particularly preferably from about 0.03 to about 1% by weight of DMAH, a sufficient effect of reducing the viscosity of the resulting composition can usually be obtained in handling DMAH at normal temperature, i.e. a viscosity of not more than about 5000 mPa.s, preferably not more than about 2000 mPa.s, more preferably not more than about 1000 mPa.s, and particularly preferably not more than about 500 mPa.s.

The Lewis base to be used can suitably be selected depending on the application of the DMAH. The Lewis bases containing oxygen generally have a better effect in reducing the viscosity. When even a very small amount of oxygen impurity exerts a deleterious influence on the use of the DMAH composition, other Lewis bases such as compounds containing at least one nitrogen atom (i.e. amines and heterocyclic compounds having at least one nitrogen atom in a ring structure) are preferably used.

A process comprising adding the Lewis base to DMAH, followed by mixing, is only shown as an example of a process for producing the DMAH composition according to the present invention. As a matter of course, the process of previously adding the Lewis base at the time of synthesizing DMAH may be used in the present invention if the amount of the Lewis base in the DMAH composition is sufficient for the purpose of reducing the viscosity.

The DMAH composition whose viscosity is reduced according to the present invention may be used as an aluminum raw material in the chemical vapor deposition process after introduction into a vapor deposition device according to a method comprising bubbling a carrier gas such as hydrogen gas in a solution comprising the DMAH composition to form a vapor of DMAH, or a method comprising heating a solution comprising the DMAH composition in an evaporator to evaporate DMAH and supplying a carrier gas therein.

The method for evaporating the DMAH composition, method for introducing it into the vapor deposition device, method for using it in the vapor deposition device and devices used for these methods may be methods or devices which have hitherto been known, and are not specifically limited.

As described above, the DMAH composition of the present invention has a viscosity of not more than about 5000 mPa.s at normal temperature, normally not more than about 2000 mPa.s, preferably not more than about 1000 mPa.s, which is superior in handling properties. The viscosity of DMAH can be easily reduced by an extremely simple operation of adding a very small amount of a Lewis base to DMAH. Therefore, the industrial utility value of the DMAH composition as the aluminum raw material in the chemical vapor deposition process is quite significant.

The following Examples and Comparative Example further illustrate the present invention in detail but are not to be construed to limit the scope thereof.

In the present invention, analysis of concentration of ether in DMAH and viscosity analysis of DMAH were conducted by the method described below.

Analysis of ether: After DMAH was diluted with dodecane, the resulting solution was hydrolyzed. Then, the content of the ether (diethyl ether and THF) in water, dodecane and gas were respectively determined by gas chromatography, and the content was converted into the ether concentration to DMAH. As the amount of the ether calculated by the above analysis was found to be identical to the amount actually added, all of the amounts of Lewis base in the Examples and of heptane in the Comparative Example are shown by the amounts added.

Viscosity analysis of DMAH: After DMAH as a sample was supplied to one of two containers connected to each other with a capillary, an inert gas was introduced into this container under pressure and transferred to another container. At this point, the transfer amount and time were measured, and then they were substituted into the Poiseuille's equation to determine viscosity.

EXAMPLE 1

Diethyl ether was added to commercially available DMAH (17 g) (manufactured by Sumitomo Chemical Industries Co., Ltd., viscosity: 7700 mPa.s, purity of 99.999% calculated from inorganic material analysis) in the amount shown in Table 1 and, after stirring with a magnetic stirrer, the viscosity of the resulting DMAH composition was measured at room temperature (25° C.). The results are shown in Table 1.

TABLE 1

| Experiment No. | Amount of diethyl ether added (% by weight/DMAH) | Viscosity of DMAH composition |
| --- | --- | --- |
| 1 | None | 7700 |
| 2 | 0.09 | 300 |
| 3 | 0.13 | 180 |
| 4 | 0.64 | 45 |
| 5 | 4.29 | 19 |

The amount of diethyl ether added is represented by % by weight based on DMAH.

EXAMPLE 2

According to the same manner as that described in Example 1 except for adding THF in place of diethyl ether in the amount shown in Table 2, the mixture was stirred with a magnetic stirrer, and then the viscosity of the resulting DMAH composition was measured at room temperature (25° C.). The results are shown in Table 2.

TABLE 2

| Experiment No. | Amount of THF added (% by weight/DMAH) | Viscosity of DMAH composition |
| --- | --- | --- |
| 1 | None | 7700 |
| 2 | 0.005 | 4700 |
| 3 | 0.03 | 1200 |
| 4 | 0.15 | 135 |

EXAMPLE 3

According to the same manner as that described in Example 1 except for adding triethylamine in place of diethyl ether in the amount shown in Table 3, the mixture was stirred with a magnetic stirrer, and then the viscosity of the resulting DMAH composition was measured at room temperature (25° C.). The results are shown in Table 3.

TABLE 3

| Experiment No. | Amount of triethylamine added (% by weight/DMAH) | Viscosity of DMAH composition |
| --- | --- | --- |
| 1 | None | 7700 |
| 2 | 0.14 | 1100 |
| 3 | 0.71 | 140 |

Comparative Example 1

According to the same manner as that described in Example 1 except for adding heptane in place of diethyl ether in the amount shown in Table 4, the mixture was stirred with a magnetic stirrer, and then the viscosity of the resulting DMAH composition was measured at room temperature (25° C.). The results are shown in Table 4.

TABLE 4

| Experiment No. | Amount of heptane added (% by weight/DMAH) | Viscosity of DMAH composition |
| --- | --- | --- |
| 1 | None | 7700 |
| 2 | 2.9 | 5600 |
| 3 | 17.1 | 1500 |
| 4 | 31.4 | 640 |

EXAMPLE 4

N,N-dimethylaniline was added to commercially available DMAH (17 g) (manufactured by Sumitomo Chemical Industries Co., Ltd., viscosity: 10000 mPa.s, purity of 99.999% calculated from inorganic material analysis) in the amount shown in Table 5 and, after stirring with a magnetic stirrer, the viscosity of the resulting DMAH composition was measured at room temperature (25° C.). The results are shown in Table 5.

TABLE 5

| Experiment No. | Amount of N,N-dimethylaniline (% by weight/DMAH) | Viscosity of DMAH composition |
| --- | --- | --- |
| 1 | None | 10000 |
| 2 | 0.10 | 860 |
| 3 | 0.25 | 220 |

EXAMPLE 5 TO 7

According to the same manner as that described in Example 4 except for adding a Lewis base in place of N,N-dimethylaniline in the amount shown in Table 6, the mixture was stirred with a magnetic stirrer, and then the viscosity of the resulting DMAH composition was measured at room temperature (25° C.). The results are shown in Table 6.

TABLE 6

| Example No. | Kind of Lewis base added | Amount (% by weight/DMAH) | Viscosity of DMAH composition |
| --- | --- | --- | --- |
| 5 | diethyl ether | 0.008 | 3000 |
| 6 | dimethyl-dodecylamine | 0.071 | 4000 |
| 7 | dimethylaniline | 0.048 | 3700 |
| control | None | None | 10000 |

What is claimed is:

1. A dimethylaluminum hydride composition comprising dimethylaluminum hydride and at least one Lewis base in an amount of from about 0.001 to about 10% by weight based on the dimethylaluminum hydride.

2. The dimethylaluminum hydride composition according to claim 1, wherein the amount of the Lewis base is from about 0.005 to about 10% by weight based on dimethylaluminum hydride.

3. The dimethylaluminum hydride composition according to claim 1, wherein the amount of the Lewis base is from about 0.01 to about 10% by weight based on dimethylaluminum hydride.

4. The dimethylaluminum hydride composition according to claim 1, wherein the amount of the Lewis base is from about 0.03 to about 1% by weight based on dimethylaluminum hydride.

5. The dimethylaluminum hydride composition according to claim 1, wherein the viscosity is not more than about 5000 mPa.s at 25° C.

6. The dimethylaluminum hydride composition according to claim 5, wherein the viscosity is not more than about 2000 mPa.s at 25° C.

7. The dimethylaluminum hydride composition according to claim 5, wherein the viscosity is not more than about 1000 mPa.s at 25° C.

8. The dimethylaluminum hydride composition according to claim 5, wherein the viscosity is not more than about 500 mPa.s at 25° C.

9. The dimethylaluminum hydride composition according to claim 1, wherein the Lewis base is an organic compound containing at least one element selected from Groups Vb and VIb in the Periodic Table.

10. The dimethylaluminum hydride composition according to claim 1, wherein the Lewis, base is an organic compound containing at least one element selected from the group consisting of N, P, As, O and S.

11. The dimethylaluminum hydride composition according to claim 1, wherein the Lewis base is selected from the group consisting of diethyl ether, dibutyl ether, methyl butyl ether, anisole, diphenyl ether, benzyl ether, dimethoxyethane, diethoxyethane, tetrahydrofuran, dioxane, triethylamine, trioctylamine, dimethylpropylamine, dimethyldodecylamine, dimethylaminotrimethylsilane, dimethylallylamine, diisopropylethylamine, dimethylaniline, benzylethylaniline, tetramethylethylenediamine, tetramethyldiaminopropane, tetramethylhexamethylenediamine, pyridine, dimethylaminopyridine, collidine, pyrazine, dimethylpyrazine, pyrazole, quinoline, isoquinoline, triazine, triazole, quinaldine, imidazole, benzylmethylimidazole, dimethyl sulfide, diethyl sulfide, diphenyl sulfide, thiophene, triethylphosphine, triphenylphosphine and triethylarsine.

12. The dimethylaluminum hydride composition according to claim 11, wherein the Lewis base is selected from the group consisting of diethyl ether, dibutyl ether, tetrahydrofuran, triethylamine, dimethyldodecylamine and dimethylaniline.

13. A process for producing a dimethylaluminum hydride composition having a viscosity of not more than about 5000 mPa.s at 25° C., which comprises adding at least one Lewis base to dimethylaluminum hydride in an amount of from about 0.001 to about 10% by weight of the dimethylaluminum hydride.

14. A method of reducing the viscosity of dimethylaluminum hydride to not more than about 5000 mPa.s which comprises adding at least one Lewis base to dimethylaluminum hydride in an amount of about 0.001 to about 10% by weight of the dimethylaluminum hydride.

15. The method according to claim 14, wherein the amount of the Lewis base is from about 0.005 to about 1% by weight based on the dimethylaluminum hydride.

16. The method according to claim 14, wherein the amount of the Lewis base is from about 0.01 to about 1% by weight based on the dimethylaluminum hydride.

17. The method according to claim 14, wherein the amount of the Lewis base is from about 0.03 to about 1% by weight based on the dimethylaluminum hydride.

18. The method according to claim 14, wherein the viscosity is not more than about 2000 mPa.s at 25° C.

19. The method according to claim 14, wherein the viscosity is not more than about 1000 mPa.s at 25° C.

20. The method according to claim 14, wherein the viscosity is not more than about 500 mPa.s at 25° C.

21. The method according to claims 14, wherein the Lewis base is an organic compound containing at least one element selected from Groups Vb and VIb in the Periodic Table.

22. The method according to claim 14, wherein the Lewis base is an organic compound containing at least one element selected from the group consisting of N, P, As, O and S.

23. The method according to claim 14, wherein the Lewis base is selected from the group consisting of diethyl ether, dibutyl ether, methyl butyl ether, anisole, diphenyl ether, benzyl ether, dimethoxyethane, diethoxyethane, tetrahydrofuran, dioxane, triethylamine, trioctylamine, dimethylpropylamine, dimethyldodecylamine, dimethylaminotrimethylsilane, dimethylallylamine, diisopropylethylamine, dimethylaniline, benzylethylaniline tetramethylethylenediamine, tetramethyldiaminopropane, tetramethylhexamethylenediamine, pyridine, dimethylaminopyridine, collidine, pyrazine, dimethylpyrazine, pyrazole, quinoline, isoquinoline, triazine, triazole, quinaldine, imidazole, benzylmethylimidazole, dimethyl sulfide, diethyl sulfide, diphenyl sulfide, thiophene, triethylphosphine, triphenylphosphine and triethylarsine.

24. The method according to claim 23, wherein the Lewis base is selected from the group consisting of diethyl ether, dibutyl ether, tetrahydrofuran, triethylamine, dimethyldodecylamine and dimethylaniline.

\* \* \* \* \*